(12) United States Patent
Denissen et al.

(10) Patent No.: US 11,253,168 B2
(45) Date of Patent: Feb. 22, 2022

(54) METHODS AND SYSTEMS FOR VISUALIZING SHAPES OF TRACKED DEVICES

(71) Applicant: KONINKLIJKE PHILIPS N.V., Eindhoven (NL)

(72) Inventors: Sander Hans Denissen, Best (NL); Wilhelmus Henrica Gerarda Maria Van Den, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 812 days.

(21) Appl. No.: 15/773,212

(22) PCT Filed: Nov. 28, 2016

(86) PCT No.: PCT/EP2016/078924
§ 371 (c)(1),
(2) Date: May 3, 2018

(87) PCT Pub. No.: WO2017/089603
PCT Pub. Date: Jun. 1, 2017

(65) Prior Publication Data
US 2018/0317806 A1    Nov. 8, 2018

(30) Foreign Application Priority Data

Nov. 26, 2015    (EP) .................................... 15196511

(51) Int. Cl.
*A61B 5/06* (2006.01)
*A61B 34/20* (2016.01)
*A61M 25/01* (2006.01)

(52) U.S. Cl.
CPC .............. *A61B 5/066* (2013.01); *A61B 5/065* (2013.01); *A61B 34/20* (2016.02); *A61M 25/01* (2013.01); *A61B 2034/2061* (2016.02)

(58) Field of Classification Search
CPC . A61B 5/066; A61B 2034/2061; A61M 25/01
See application file for complete search history.

(56) References Cited

U.S. PATENT DOCUMENTS

2012/0249551 A1    10/2012  Chernoff
2014/0088413 A1 *   3/2014  Von Bucsh ............ A61B 5/061
                                                 600/424

(Continued)

*Primary Examiner* — Alexandra L Newton
*Assistant Examiner* — Rynae Boler (57) ABSTRACT

The present invention relates to a method and system of visualizing a first sensed shape of a first elongated device (14) having a first) length and a second sensed shape of a second elongated device (16) having a second length. The first elongated device (14) and the second elongated device (16) are physically linked to one another over at least a part (28) of the first and second lengths. The first sensed shape and the second sensed shape have been obtained independently of each other. The method comprises the steps: providing one of the first and second sensed shapes as a reference shape and the other of the first and second sensed shapes as a linked shape; determining along the reference shape and the linked shape an overlap region in which the reference shape and the linked shape should match due to a physical overlap of the first and second elongated devices (14, 16) in this region; copying, in the overlap region, an overlap region reference shape portion to an overlap region linked shape portion so that, in the overlap region, the linked shape is visualized as matching the reference shape.

20 Claims, 6 Drawing Sheets (56) References Cited

U.S. PATENT DOCUMENTS

| | | | |
|---|---|---|---|
| 2014/0114180 A1* | 4/2014 | Jain | A61B 6/12 600/424 |
| 2015/0254526 A1 | 9/2015 | Denissen | |
| 2016/0102969 A1 | 4/2016 | Verstege et al. | |
| 2016/0157939 A1 | 6/2016 | Larkin | |
| 2016/0213432 A1 | 7/2016 | Flexman et al. | |

* cited by examiner

METHODS AND SYSTEMS FOR VISUALIZING SHAPES OF TRACKED DEVICES

CROSS-REFERENCE TO PRIOR APPLICATIONS

This application is the U.S. National Phase application under 35 U.S.C. § 371 of International Application Serial No. PCT/EP2016/078924, filed on Nov. 28, 2016, which claims the benefit of European Patent Application No. 15196511.8, filed on Nov. 26, 2015. This application is hereby incorporated by reference herein.

FIELD OF THE INVENTION

The present invention relates to methods and systems for visualizing shapes of shape sensed elongated devices, wherein the elongated devices are at least partially physically linked to one another, while the elongated devices are shape sensed independently of each other.

BACKGROUND OF THE INVENTION

The shapes of elongated devices can be sensed by different shape sensing technologies, for example magnetic resonance imaging (MRI) or computer tomography (CT). Another shape sensing technology for sensing the shapes of elongated devices is referred to as Fiber-Optic RealShape (FORS). In the present description, reference is particularly made to FORS as the preferred shape sensing technology, but it is to be understood that the present invention is not limited thereto.

With FORS using an optical shape sensing fiber integrated in an elongated device, the three-dimensional shape of the device can be known and thus be made "visible" up to the tip of the device, although the device itself may be invisible for the user's eyes. In medical applications, FORS fibers can be integrated into a wide range of elongated medical devices like catheters, guidewires or endoscopes to provide live guidance or navigation of medical procedures. It is to be understood that the present invention is not limited to medical applications, but can be also widely used in industrial fields of technology.

With FORS, two or more elongated devices can be tracked simultaneously. In this case, each of the tracked devices is equipped with a FORS fiber. The optical fibers of the individual devices are interrogated simultaneously, and the 3D shape of each of the devices can be reconstructed, accordingly. The reconstructed shapes can be visualized together on a display or screen of a monitor.

In certain applications, two or more elongated devices are physically linked to each other over at least a part of their length. For example, considering a guidewire and a catheter as used in medical applications, the guidewire is at least partially inserted in the catheter. Thus, in the "physical world", the guidewire and the catheter are almost perfectly aligned with each other in the region where the guidewire runs through the catheter. When the guidewire and the catheter are tracked independently of each other by FORS, the reconstructed shapes of the guidewire and the catheter should be visualized as being perfectly aligned in the region of the physical overlap of the guidewire and catheter. However, in practice, it may happen that the visualized reconstructed 3D shapes of the guidewire and the catheter are not perfectly aligned in the overlap region. Small errors in the shape sensing accuracy, for example in the localization of the sensed shapes with respect to the coordinate system of the shape sensing system can result in a misaligned visualization of the tracked devices in regions where the sensed shapes should match. If, for example, the devices are rendered as a mesh tube, the mesh tubes will not align but intersect each other at several points in the visualized reconstructed shapes. In particular, in a live video guidance and navigation procedure, such misalignments in the visualization may temporally vary leading to an unstable rendering of the sensed shapes, leading to distraction and tiring of the user.

In summarizing the foregoing, when two or more devices are tracked independently of each other, but are physically linked, for example one device is arranged inside the other, visualization by simply drawing the individual shapes will produce an unstable image.

WO 2015/049612 A2 discloses an optical shape sensing hub to maintain two or more tracked devices in a fixed geometrical configuration relative to one another such that distally to the hub the two or more devices have shaped sensed reconstruction data registered therebetween. The hub has specific mechanical features for generating a hub template of an expected shape of the hub in the shape data, wherein measured shape data are searched to match the hub template to determine a hub position in the shape data, wherein a registration between the two or more devices is determined by finding an overlap in the shape data relative to the hub position.

WO2014/207182 A1 describes a method and system capable of providing high precision 3D optical shape sensing over a length exceeding what is possible with a single fiber. To this end, a second fiber is mechanically concatenated to the first optical fiber and shape sensing of the second fiber is registered to the coordinate space of the first fiber. In particular to increase the length of the shape sensing functionality, a proximal portion of the second fiber is registered to a distal portion of the first fiber.

SUMMARY OF THE INVENTION

It is an object of the present invention to provide a method and a system for improved visualization of reconstructed shapes of two or more independently tracked devices which are at least partially physically linked to each other.

In a first aspect of the present invention, a method of visualizing a first sensed shape of a first elongated device having a first length and a second sensed shape of a second elongated device having a second length is provided, the first elongated device and the second elongated device being physically linked to one another over at least a part of the first and second lengths, the first sensed shape and the second sensed shape having been obtained independently of each other, comprising the steps:

i) providing one of the first and second sensed shapes as a reference shape and the other of the first and second sensed shapes as a linked shape;

ii) determining along the reference shape and the linked shape an overlap region in which the reference shape and the linked shape should match due to a physical overlap of the first and second elongated devices in this region;

iii) copying, in the overlap region, an overlap region reference shape portion to an overlap region linked shape portion so that, in the overlap region, the linked shape is visualized as matching the reference shape.

The visualization method according to the invention uses one of the first and second sensed shapes of the first and second elongated devices as reference shape and the other one as linked shape. Sensed shape is to be understood as the shape data as provided by a shape sensing system. Which one of the first and second sensed shapes is treated as the reference shape and which one is treated as the linked shape is not decisive in the visualization method according to the invention, as long as this allocation is maintained during the method. With respect to the above example of a guidewire and a catheter, the sensed shape of the guidewire can be used as the reference shape and the sensed shape of the catheter as the linked shape, but also vice versa. The strategy to determine the reference shape can be based on a) known stability of the device type, b) system configuration, c) user choice, d) known stability of specific fiber type, e) known stability during use within a procedure, f) known intended use of the device (e.g. fiber is inside reference catheter which is known not to move much, or in thicker endoscope), etc., or a combination of the above.

In the method according to the invention, the reference shape and the linked shape are processed in order to determine an overlap region of overlap of the first sensed shape with the second sensed shape. The overlap region is the region where the visualized sensed shapes should match, for example should be coincident in the display or monitor image. Determining the overlap region can be done, for example, from prior registration information, knowledge of where the elongated devices can physically overlap and the 3D registered position of each point along the sensed shapes. In the example of a guidewire which is partially inserted in a catheter, the overlap region is the part of the length of the guidewire which runs through the catheter.

Finally, when the overlap region has been determined, the reference shape is copied to the linked shape in the overlap region so that, in the overlap region, the linked shape is visualized as matching the reference shape. It is also possible to say that the linked shape in the overlap region is replaced with the reference shape in the overlap region, thus avoiding that the shapes of the elongated devices are visualized on the display or monitor as not perfectly aligned shapes in the region of physical overlap of the devices.

The visualization method according to the invention does not require a specific hub template for achieving an improved visualization.

Within the scope the present invention, the sensed shapes of the elongated devices can be obtained by any shape sensing technology, for example magnetic resonance imaging (MRI) or computer tomography (CT), which is suitable for 3D shape reconstruction. In particular, the shapes of the elongated devices can be sensed by optical shape sensing (FORS). In the present description, reference is made to FORS as the shape sensing technology, but it is to be understood that the present invention is not limited thereto.

Preferred embodiments of the visualization method according to the invention are defined in the dependent claims.

In a preferred refinement, step iii) further comprises adding linked shape portions outside the overlap region to the overlap region reference shape portion to provide a full length visualization of the linked shape.

In a further preferred refinement, a Procrustes-based coordinate transformation of the linked shape is performed. This can be done by taking overlapping reference and linked shape points, calculating a Procrustes matrix, and applying the matrix to the linked shape points. Using a Procrustes transformation ensures a minimal misalignment in terms of orientation, thus limiting the orientational inaccuracy of the linked shape. If the overlap region length is not known, a 'safe' number of points can be used for the Procrustes registration, starting from the overlap region start, and, if required, the optimal registration and overlap region length is determined. In a further refinement, the Procrustes transformation could be done every n shape updates to limit the number of calculations, or triggered by a check of the registration validity. To this end, and in the simplest form, the distance between the tip of the non-extending shape to the other shape can be used.

Thus, a full and continuous visualization of the linked shape is obtained.

In particular in the context of the preceding refinement, step ii) further comprises determining a tip shift vector, if a linked shape tip of the linked shape protrudes beyond a reference shape tip of the reference shape, and step iii) further comprises translating a linked shape tip portion of the linked shape according to the tip shift vector.

This measure ensures that, in case the linked shape sticks out of or protrudes beyond the reference shape tip, there are no discontinuities in the visualization of the linked shape in the transition from the overlap region to the protruding tip portion of the linked shape.

Further preferably, step i) can further comprise calculating a smallest first distance from a tip of the reference shape to the linked shape, and calculating a smallest second distance from a tip of the linked shape to the reference shape.

This refinement can be advantageously used for several purposes. For example, the results of these calculations can be used for determining whether the tip of the linked shape sticks out of or protrudes beyond the tip of the reference shape, or whether the tip of the linked shape is within the reference shape, and/or for determining, whether the sensed shapes of the devices actually have an overlap region or not.

In the context of the latter, at least step iii) is not carried out, if a smaller one of the smallest first and second distances is above a predetermined error threshold. This advantageously avoids that parts of the first and second sensed shapes are matched with one another while the corresponding physical parts of the devices actually do not match.

Further preferably, step ii) further comprises determining a linked shape hub point index along the linked shape as a proximal starting point index of the overlap region with respect to the linked shape, and determining a reference shape hub point index as a proximal starting point index of the overlap region with respect to the reference shape.

The determination of the linked shape hub point index and the reference shape hub point index is advantageous to determine the overlap region of overlap of the first and second sensed shapes in very precise manner with a maximum error within one index. The hub point is the point along the elongated devices where, seen from the proximal end of the devices, the physical overlap starts. The shared or overlap region with respect to the linked shape ranges from the linked shape hub point index to the distal tip of the linked shape (if the linked shape is within the reference shape). The reference shape point index is advantageous for knowing the reference shape points at which the reference shape information is to be used for step iii), namely for copying the reference shape to the linked shape.

In connection with the preceding refinement, the reference shape hub point index may be calculated as a difference between the linked shape hub point index and an index offset, wherein the index offset can be calculated according to one of the following equations:

a) index offset=second length−1−index of $P_{Ref}$ b) index offset=index of $P_{Linked}$−first length+1, wherein $P_{Ref}$ is the point on the reference shape according to the smallest second distance, and $P_{Linked}$ is the point on the linked shape according to the smallest first distance.

This refinement provides a simple calculation scheme for determining the reference shape hub point index from the linked shape hub point index using the index offset which is the difference between the reference shape hub point index and the linked shape hub point index. The afore-mentioned calculation scheme enables a very precise calculation of the reference shape hub point index with a maximum tolerance of one index, if the distance between indices is constant and the same for the sensed shapes.

It is to be noted that, in particular in FORS, shape sensing of a device along the length of the device is discretized according to indices along the length of the device, or to be exact, along the optical fiber which is optically interrogated.

Further preferably, before carrying out step iii), the method comprises checking whether all points of the linked shape in the overlap region determined in step ii) fall within the array size of the linked shape.

This refinement advantageously increases the reliability of the visualization method according to the invention, because if the afore-mentioned check is negative, matching of the linked and reference shape will not be performed.

In a further refinement, the visualization method according to the invention further comprises, before carrying out step iii), checking whether at least a part of the linked shape is within a threshold distance from the reference shape.

This refinement advantageously also increases the reliability of the visualization method according to the invention, because if the afore-mentioned check is negative, it can be concluded that the linked and reference shapes do not actually overlap so that a matching of shapes that are not actually aligned with each other can be excluded. For example, it can happen that the elongated devices have their tips close to each other, while the remaining portions of the two devices are spaced apart from one another and not physically linked. In this case, the shapes of the devices should not be visualized as matching shapes.

In a second aspect of the present invention, a visualizing system for visualizing a first sensed shape of a first elongated device having a first length and a second sensed shape of a second elongated device having a second length is provided, the first elongated device and the second elongated device being physically linked to one another over at least a part of the first and second lengths, the visualizing system being configured to:

i) use one of the first and second sensed shapes as a reference shape and the other of the first and second sensed shapes as a linked shape;

ii) determine along the reference shape and the linked shape an overlap region in which the reference shape and the linked shape should match due to a physical overlap of the first and second elongated devices in this region;

iii) copy, in the overlap region, an overlap region reference shape portion to an overlap region linked shape portion so that, in the overlap region, the linked shape is visualized as matching the reference shape.

It shall be understood that the claimed visualizing system has similar and/or identical advantages as the visualization method according to the invention, and that the claimed visualizing system has similar and/or identical preferred refinements as the claimed method and as described above.

In a third aspect of the present invention, a system is provided, comprising:

a first elongated device having a first length and a second elongated device having a second length, the first elongated device and the second elongated device being physically linked to one another over at least a part of the first and second lengths;

a shape sensing system for individually shape sensing the first elongated device and the second elongated device to provide a first sensed shape of the first elongated device and a second sensed shape of the second elongated device; and a visualizing system according to the second aspect.

Again, the advantages and above preferred refinements described with respect to the visualization method according to the invention hold for the claimed system according to the third aspect.

The shape sensing system is preferably configured as an optical shape sensing system.

The optical shape sensing system preferably comprises a first optical fiber associated with the first elongated device, and a second optical fiber associated with the second elongated device, wherein the shape sensing system interrogates the first and second optical fibers independently from one another.

In a preferred refinement, one of the first and second elongated devices is a catheter, and the other one is a guidewire at least partially inserted into the catheter.

In a still further aspect, a computer program is provided comprising program code means for causing a computer to carry out the steps of the claimed visualization method according to the first aspect, when said computer program is carried out on a computer.

It shall be understood, that the visualization method and system according to the invention also can work with more than two elongated devices which are shape sensed independently of one another, but mutually physically linked over at least part of their lengths.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
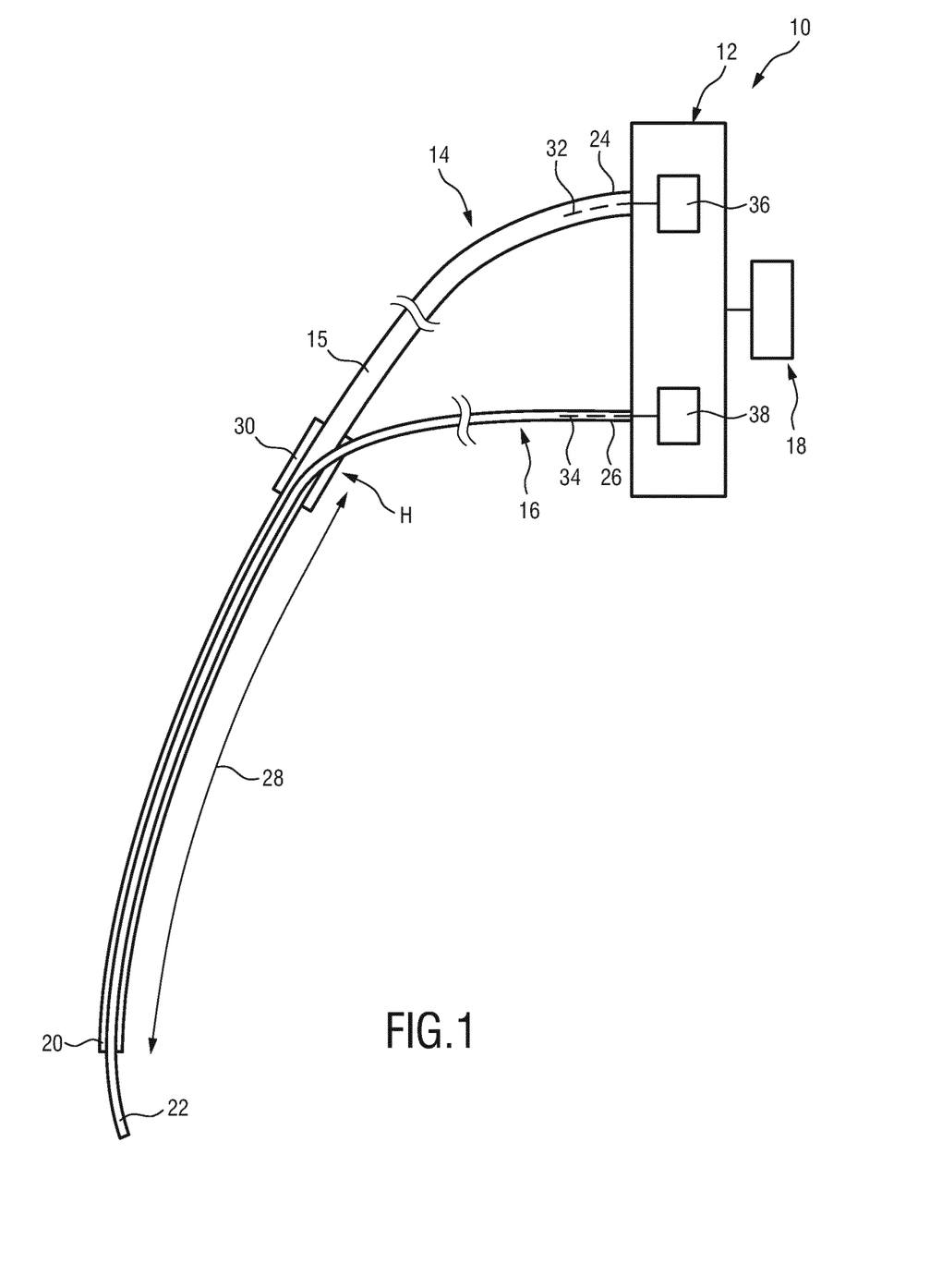
FIG. 1 shows an overall view of a system including a shape sensing system, elongated devices and a visualizing system.

FIG. 1 generally shows a system 10 comprising a shape sensing system 12, a first elongated device 14, a second elongated device 16 and a visualizing system 18. Without restricting generality, the system 10 is a medical system. The first elongated device 14 can be a catheter 15, and the second elongated device 16 can be a guidewire 17.

The first elongated device 14 has a distal tip 20, and the second elongated device 16 has a distal tip 22. The first elongated device 14 has a proximal end 24, and the second elongated device has a proximal end 26. The first elongated device 14 has a first length from the proximal end 24 to the distal tip 20, and the second elongated device 16 has a second length from the proximal end 26 to the distal tip 22. Over at least a part of the first and second lengths of the first elongated device 14 and the second elongated device 16, the first and second elongated devices 14, 16 are physically linked to one another. The common part of the first and second lengths over which the first and second elongated devices 14, 16 are physically linked, is denoted with reference numeral 28 in FIG. 1. The common part 28 defines an overlap region of overlap of the first and second devices 14, 16. In the present embodiment, the second elongated device 16 is partially inserted into the first elongated device 14 and runs through the common part 28. In the exemplary situation shown in FIG. 1, the tip 22 of the second elongated device 16 sticks out or protrudes beyond the tip 20 of the first elongated device. During use of the first and second elongated devices 14, 16, it is also possible to displace the first and second elongated devices 14, 16 relative to one another in longitudinal direction, i.e. in direction of their lengths.

A hub 30 serves for interconnecting the first and second devices 14, 16. A hub point H defines the location along the lengths of the first and second devices 14, 16 at which, seen in direction from the proximal ends 24, 26 to the distal tips 20, 22, the physical linking or overlap of the first and second elongated devices 14, 16 starts. In the case where the first elongated device 14 is a catheter 15 and the second elongated device 16 is a guidewire 17, the part of the catheter extending from the proximal end to the hub point H is also referred to as catheter torque absorbing section (the catheter torque absorbing section is the section of the catheter which is used for maneuvering or manipulating the catheter), and the part of the guidewire extending from the proximal end to the hub point H is also referred to as the guidewire lead-in section.

In an embodiment, the shape sensing system 12 is configured as a Fiber-optic RealShape (FORS) system. As such, the FORS system comprises a first optical fiber 32 associated with the first elongated device 14. The optical fiber 32 extends through the first elongated device 14 from the proximal end 24 to the distal tip 20. The optical shape sensing system 12 further comprises a second optical fiber 34 associated with the second elongated device 16 and extending through the second elongated device 16 from the proximal end 26 to the distal tip 22. In order to simplify the drawing, the optical fibers 32 and 34 are only shown in the region of the proximal ends 24 and 26 of the devices 14 and 16.

The optical fibers 32 and 34 may be any type of optical fiber suitable for optically sensing the elongated devices 14 and 16. Examples of the optical fibers 32 and 34 include, but are not limited to a flexible optically transparent glass or plastic fiber incorporating an array of fiber Bragg gratings as known in the art, and a flexible optically transparent glass or plastic fiber having naturally variations in its optic refractive index occurring along the fiber as known in the art (e.g., Rayleigh scattering based optical fiber). The optical fibers 32, 34 may be single-core fibers or, preferably, multi-core fibers.

The shape sensing system 12 comprises first shape sensing components and circuitry 36 for shape sensing the first elongated device 14 via the first optical fiber 32, and second shape sensing components and circuitry 38 for shape sensing the second elongated device 16 via the second optical fiber 34. The first elongated device 14 and the second elongated device 16 are shape sensed simultaneously, but independently of one another by the shape sensing system 12.

It is to be understood that the shape sensing system 12 can be configured to sense the shape of more than two elongated devices simultaneously.

In the present embodiment according to which the shape sensing system 12 is a FORS system, the first and second shape sensing components and circuitries 36, 38 may include, in each case, a tunable light source emitting light for interrogating the optical fibers 32, 34, and a fiber-optic interferometer, and a shape reconstruction unit for reconstructing the 3D shape of the tracked elongated devices 14, 16.

The visualizing system 18 processes the data of the sensed shapes of the first and second elongated devices 14, 16 as sensed by the shape sensing system 12 for visualizing the first sensed shape of the first elongated device 14 and the second sensed shape of the second elongated device 16 on a display or monitor included in or connected to the visualizing system 18.

Figure 2:
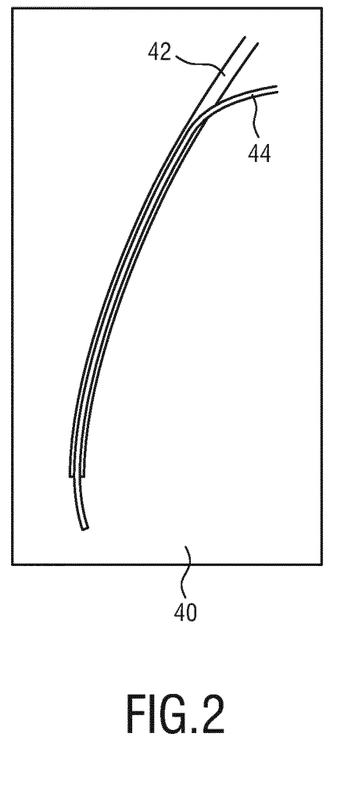
FIG. 2 shows a first visualization of a part of the shape sensed devices in FIG. 1.
Figure 3:
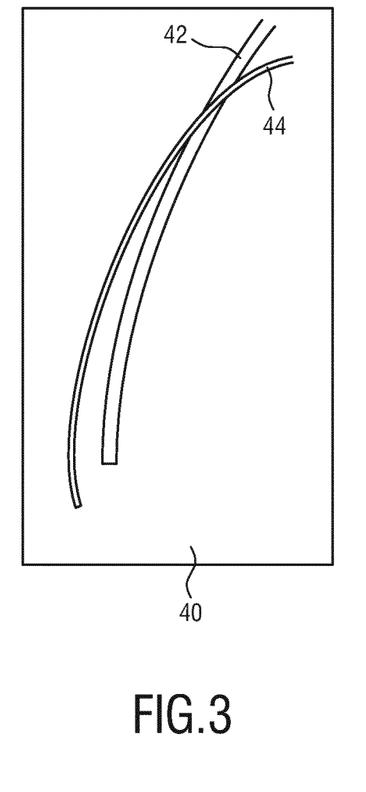
FIG. 3 shows a second visualization of the shape sensed devices in FIG. 1.

FIG. 2 shows a display 40 on which a first sensed shape 42 of the first elongated device 14 and a second sensed shape 44 of the second elongated device 16, as sensed by the shape sensing system 12, are visualized. FIG. 2 depicts an image of an ideal visualization of the sensed shapes 42 and 44 which reproduces the real shapes of the first and second elongated devices 14 and 16 as shown in FIG. 1 perfectly, in particular perfectly aligned or matched in the common part or overlap region 28 in FIG. 1. However, by simply drawing the individual sensed shapes 42 and 44, a perfect visualization of the sensed shapes 42 and 44 as shown in FIG. 2 often cannot be obtained in practice. Since the elongated devices 14 and 16 are shape sensed or tracked independently of one another, and due to inaccuracies and fluctuations of the shape sensing process performed on each of the elongated devices 14 and 16 independently of one another, it can happen that the visualization of the sensed shapes 42 and 44 can result in an unstable image in a video sequence when used during real-time navigation. This is particularly disturbing in those cases where the two tracked devices 14, 16 have parts which, in the real world, are aligned with one another as in the common part 28 shown in FIG. 1, while the visualized sensed shapes 42 and 44 are not perfectly aligned in the same part 28 as shown in FIG. 3. Please note that the visualization example in FIG. 3 is only illustrative and exaggerated. Nevertheless, even minor misalignments in the visualization of aligned parts of tracked devices can be distracting and annoying for the user.

In the following, a method is described which enables an improved visualization of sensed shapes of elongated devices by which parts of the elongated devices, which match with one another in the real world, are also visualized as matching parts of the devices on the display or monitor.

The method to be described in more detail of visualizing the first sensed shape 42 of the first elongated device 14 and the second sensed shape 44 of the second elongated device 16 is based on the idea to recalculate at least a portion of the sensed shape of one of the elongated devices 14, 16 in a region, where it should match or be aligned with the sensed shape of the other elongated device. To this end, the method is based on providing the first sensed shape as a reference shape and the second sensed shape as a linked shape; determining in the reference shape and the linked shape an overlap region of overlap of the first sensed shape with the second sensed shape; and copying, in the overlap region, the reference shape to the linked shape so that, in the overlap region, the linked shape is visualized as matching the reference shape.

An embodiment of this method will be described below in more detail with reference to FIGS. 4 to 9. The method as described below can be carried out by the visualizing system 18 of FIG. 1.

Figure 5:
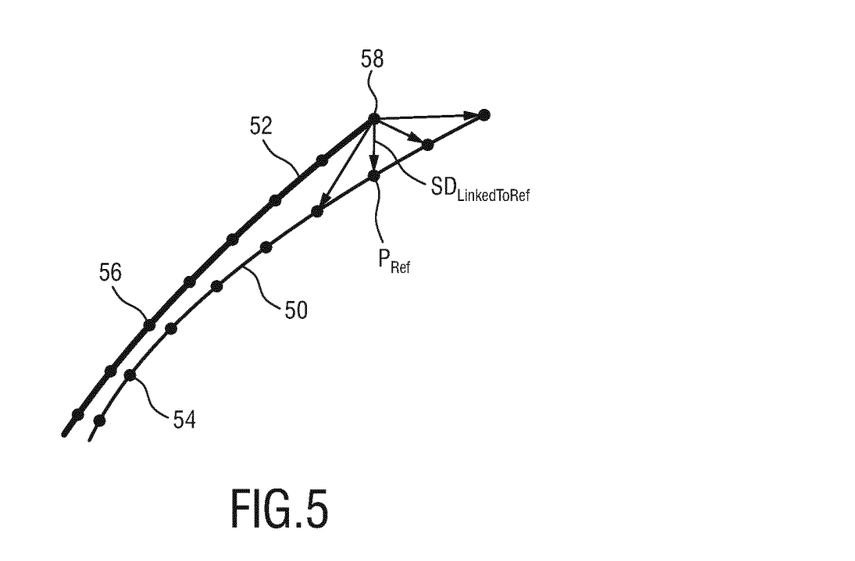
FIG. 5 illustrates a step of the method in FIG. 4.

With reference to FIG. 5, a first sensed shape 50 and a second sensed shape 52 of two independently tracked elongated devices are shown. The shown sensed shapes 50 and 52 are arbitrary examples of sensed shapes for elucidating the principles of the method to be described. The sensed shapes can be expressed as arrays of data comprising location information expressed in form of indices (e.g. 1, 2, 3, . . . , N, wherein N can be very large, e.g. >10,000, or >100,000) allocated to discrete points along the shapes, and shape information allocated to the location information. In other embodiments, the shapes could also be expressed as e.g. a 3D cardinal or Bezier spline or a Fourier series. In any case the shapes must be converted to a discrete set of triangle meshes to be rendered on a screen. The shape linking must be done prior to conversion to the 3D mesh, where the distance between points in both shapes should be the same.

The first sensed shape 50 will be designated as the reference shape hereinafter, and the second sensed shape 52 will be designated as the linked shape. The points along the reference shape 50 are denoted with reference numeral 54, and the points along the linked shape are labeled with reference numeral 56. It is to be understood that in practice the number of points 54 and points 56 is much larger than depicted in FIG. 5, and can be as large as several hundred thousands or millions along the length of the tracked devices, depending on the resolution of the shape sensing system.

Figure 4:
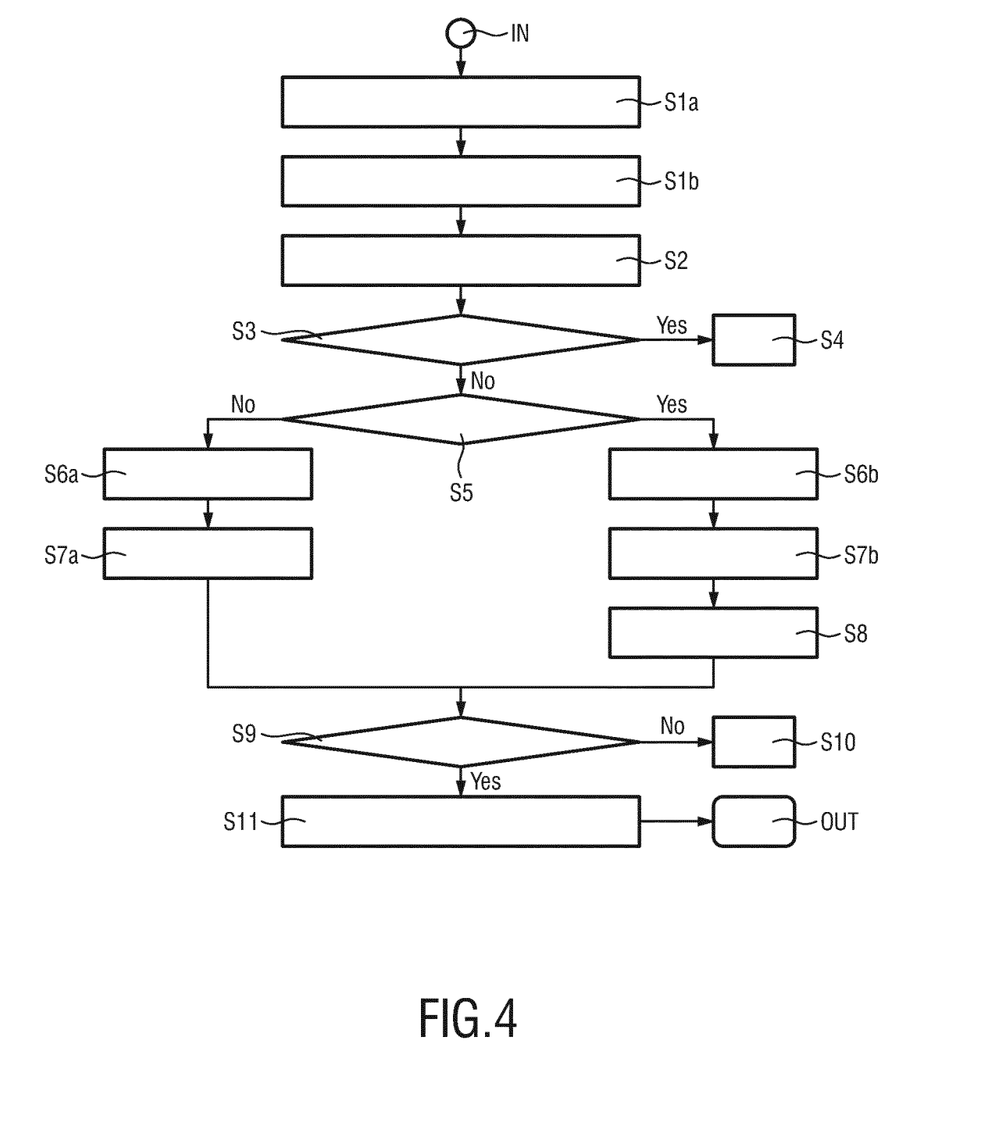
FIG. 4 shows a flow-chart of a visualization method.

With reference to FIG. 4, the method of visualizing starts at IN, where the linked shape data of the linked shape 52 and the reference shape data of the reference shape 50 are provided from the shape sensing system 12 in FIG. 1.

At S1$a$, a smallest distance $SD_{LinkedToRef}$ from a tip 58 of the linked shape 52 to all points 54 of the reference shape 50 is calculated. That point of the points 54 of the reference shape 50 which is spaced apart from the tip 58 of the linked shape 52 at the smallest distance $SD_{LinkedToRef}$ is denoted as $P_{Ref}$.

Figure 6:
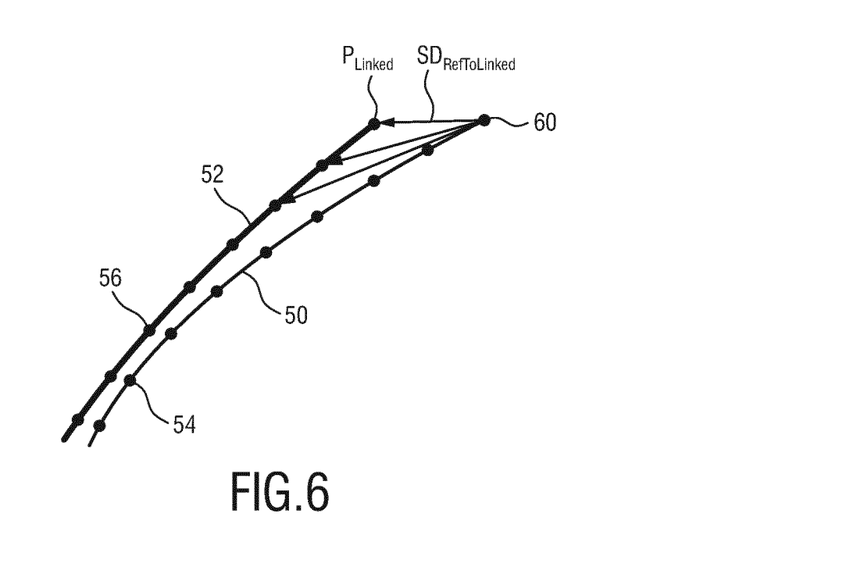
FIG. 6 illustrates a further step of the method in FIG. 4.

At S1$b$, the method according to FIG. 4 proceeds with the calculation of the smallest distance $SD_{RefToLinked}$ from a tip 60 of the reference shape 50 to all points 56 of the linked shape 52. This is illustrated in FIG. 6. That point of the points 56 of the linked shape 52 which is spaced apart from the tip 60 of the reference shape 50 at the smallest distance $SD_{RefToLinked}$ is denoted as $P_{Linked}$.

In steps S1$a$ and S1$b$, the tip direction of the reference shape 50 and the tip direction of the linked shape 52 are taken into account, and only points that are on a vector with an angle of maximally 30° with the tip direction vector are considered as candidates for the minimal distance.

After $SD_{LinkedToRef}$ and $SD_{RefToLinked}$ have been calculated, the smaller one (SD) of both is determined at S2 according to:

$$SD = Min(SD_{LinkedToRef}, SD_{RefToLinked})$$

Next, at S3, SD is compared with a specified error threshold. If SD is above this specified error threshold, the method stops at S4. If SD is above the specified error threshold, this means that the two shapes 50 and 52 are too far apart. If SD is above a warning threshold, the method will continue, but a warning state will be returned. Further explanations of error thresholds follow later.

If SD is below the error threshold the method proceeds to S5. At S5, it is determined, whether $SD_{LinkedToRef}$ is larger than or equal to $SD_{RefToLinked}$.

If $SD_{LinkedToRef} \geq SD_{RefToLinked}$, the linked shape sticks out or protrudes beyond the tip 60 of the reference shape 50 or is equal thereto. If $SD_{LinkedToRef} < SD_{RefToLinked}$, the linked shape 52 is inside the reference shape 50. The latter is shown in FIGS. 5 and 6.

In the following steps of the method, the two cases $SD_{LinkedToRef} \geq SD_{RefToLinked}$ and $SD_{LinkedToRef} < SD_{RefToLinked}$ are treated differently, and thus will be described separately.

First, the case $SD_{LinkedToRef} < SD_{RefToLinked}$ will be described. This case includes steps S6$a$ and S7$a$.

In general, steps S6$a$ and S7$a$ serve to determine an overlap region of overlap of the linked shape with the reference shape, where the linked shape and the reference shape should match due to the physical linking of the tracked devices, as for example along the common part 28 in FIG. 1. This will be explained in more detail with reference to FIG. 7.

Figure 7:
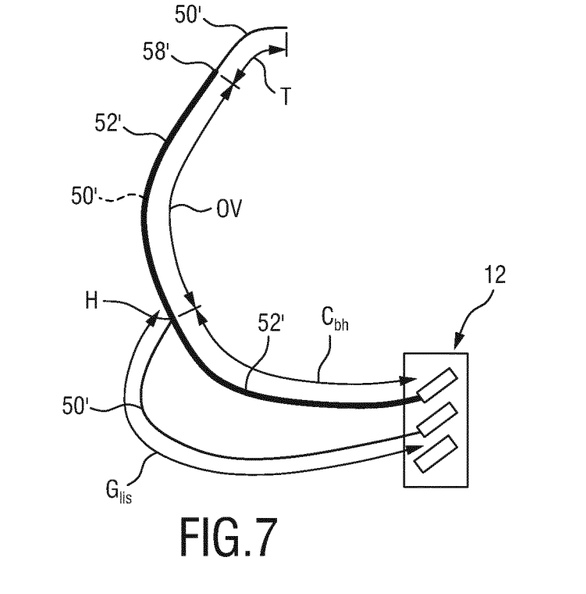
FIG. 7 illustrates a further step of the method in FIG. 4.

FIG. 7 shows sensed shapes 50' and 52', wherein 50' denotes a reference shape, and 52' denotes a linked shape. The linked shape 52' is shown as a bold line, while the reference shape 50' is shown as a thin line. In an overlap region OV, the reference shape 50' runs inside the linked shape 52'. The reference shape 50' sticks out or protrudes beyond the linked shape 52', wherein the portion of the reference shape 50' protruding from the linked shape 52' is referred to as a tip section T. Vice versa, the tip 58' of the linked shape 52' is inside the reference shape 50'.

Also shown in FIG. 7 is the shape sensing system 12 in schematic fashion.

In order to determine the overlap region OV with respect to the linked shape 52', the linked shape hub point index at the hub point H (compare FIG. 1) needs to be determined at S6 in FIG. 4, since the portion of the linked shape that is to be recalculated ranges from the computed linked shape hub point index to the tip 58' of the linked shape 52'.

The index of the linked shape hub point is the index of that point along the linked shape 52', where the overlap region OV starts with respect to the linked shape 52'.

The linked shape hub point index along the linked shape 52' can be determined, for example, as follows:

If, for example, the linked shape 52' is the sensed shape of a catheter (this case is shown in FIG. 7), for example the catheter 15 in FIG. 1, the linked shape hub point index can be determined for example by the known length $C_{bh}$ of the catheter section before hub point H, wherein the length $C_{bh}$ is sent from the shape sensing system 12, for example.

If, in another example, the linked shape 52' is the sensed shape of a guidewire, for example the guidewire 17 in FIG. 1, then the linked shape hub point index can be determined by determining the length $G_{lis}$ of the guidewire lead-in section. $G_{lis}$ is the length of the guidewire from its proximal end to the hub point H (compare FIG. 1). The length $G_{lis}$ can be computed by:

$$G_{lis} = \text{Guidewire length} - (\text{catheter length} - C_{bh} - \text{catheter tip section length})$$

The guidewire length, the catheter length, $C_{bh}$ are known quantities. Since the reference shape is the sensed shape of the catheter in this example, the catheter tip section length, or more general the reference shape tip section length, is equal to the length of the reference shape from index point $P_{Ref}$ (see FIG. 5) to the last point, which is the tip of the reference shape or a point very close thereto.

Further, at step S7a, the reference shape hub point index also needs to be determined, which is necessary to know which reference shape points to be used for copying the shape information of the reference shape 50' to the linked shape 52' in the overlap region OV.

The reference shape hub point index can be computed from the index offset between the linked shape hub point index and the reference shape hub point index. Subtracting this index offset from the just computed linked shape hub point index results in the reference shape hub point index. The index offset is computed by:

Index offset=Linked shape length−1−Index of $P_{Ref}$

Figure 8:
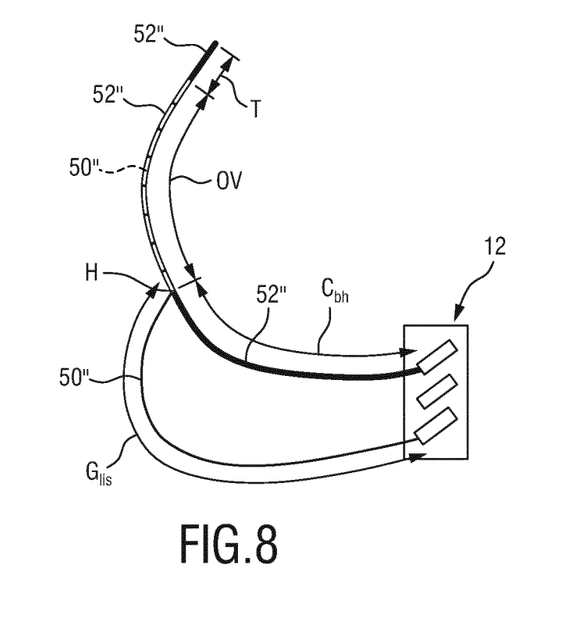
FIG. 8 illustrates a further step of the method in FIG. 4.

Now, back to step S5 in FIG. 4, the further processing of the case $SD_{LinkedToRef} \geq SD_{RefToLinked}$ will be described with reference to steps S6b, S7b, and S8 in FIG. 4 and with FIG. 8.

$SD_{LinkedToRef} \geq SD_{RefToLinked}$ means that the linked shape sticks out or protrudes beyond the reference shape. This case is shown in FIG. 8, where a reference shape 50" and a linked shape 52" are shown. The linked shape 52" is shown as a bold line, and the reference shape 50" as a thin line, wherein, in the overlap region OV which is shared by both shapes 50" and 52", both shapes 50" and 52" are shown as a double line (for a better differentiation of the tip section T of the shape 52" from the overlap region OV).

Steps S6b and S7b are similar to steps S6a and S7a described above.

In step S6b, the linked shape hub point index at hub point H has to be determined, as the overlap region OV of the linked shape 52" ranges from the linked shape hub point index to point $P_{Linked}$ (see FIG. 6).

The linked shape hub point index along the linked shape 52" can be determined as follows:

If, for example, the linked shape 52" is the sensed shape of the catheter, then the linked shape hub point index can be determined from the known length $C_{bh}$ of the catheter section before hub point, as described above.

If, in another example, the linked shape 52" is the guidewire, then the length $G_{lis}$ of the guidewire lead-in section needs to be determined. The length $G_{lis}$ can be computed by:

$G_{lis}$=Guidewire length−(catheter length−$C_{bh}$−
guidewire tip section length)

The guidewire length, the catheter length, and $C_{bh}$ are known quantities. In this example, the length of the tip section of the guidewire or more generally of the linked shape 52" is equal to the length of the linked shape 52" from point $P_{Linked}$ to the tip of the linked shape 52".

Further, according to step S7b, the reference shape hub point index at hub point H also needs to be determined, since it is necessary to know which reference shape points to use for matching the linked shape and the reference shape. For this, the index offset between the linked shape hub point index and the reference shape hub point index is computed. Subtracting this index offset from the just computed linked shape hub point index gives the reference shape hub point index. The index offset is computed by:

Index offset=Index of $P_{Linked}$−reference shape length+1.

Since in the present case the linked shape sticks out or protrudes beyond the reference shape, it is further provided to determine a tip shift vector at S8 in FIG. 4, because the linked shape along its tip section points also will need to be shifted to remain aligned when the shared points in the overlap region OV are matched. The calculation of the tip shift vector will be explained with reference to FIG. 9.

Figure 9:
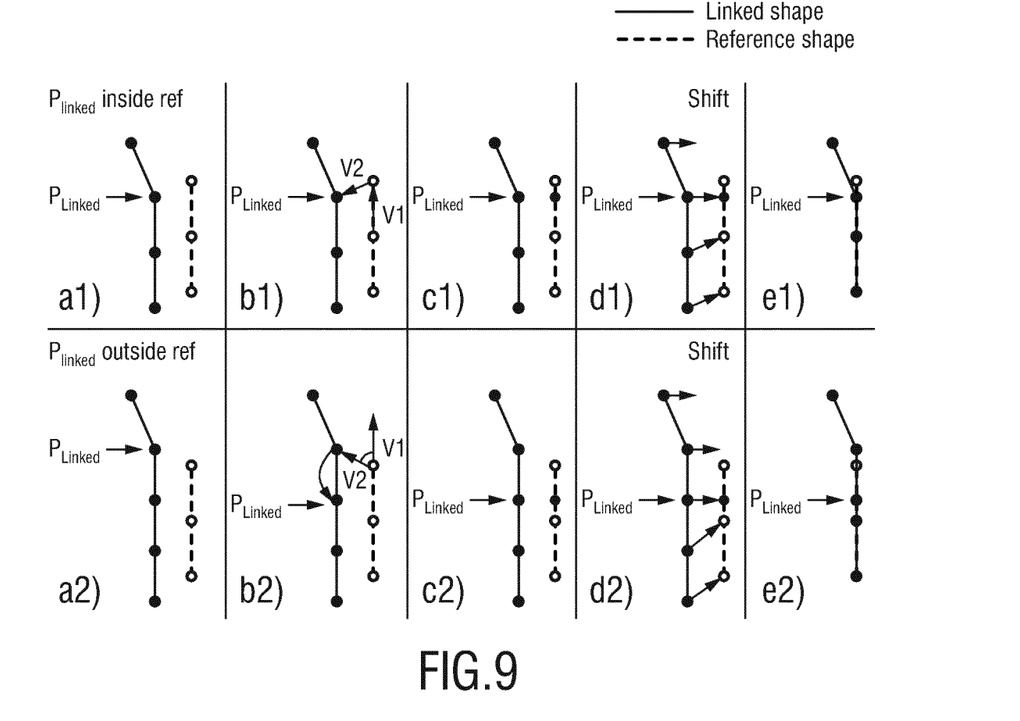
FIG. 9 illustrates a further step of the method in FIG. 4.

FIG. 9 shows in solid lines a linked shape, and in broken lines a reference shape.

The single diagrams a1) to e1) of FIG. 9 illustrate a case where the point $P_{Linked}$ as determined in step S1b is inside the reference shape, as shown in diagram a1). $P_{Linked}$ is inside the reference shape, if the angle between vector V1 and vector V2 is greater than 90°, as shown in diagram b1) of FIG. 9. Diagrams a2) to e2) in FIG. 9 instead illustrates a case where the point $P_{Linked}$ on the linked shape is outside the reference shape. In this case the angle between the vector V1 and the vector V2 is smaller than 90° (diagram b2)). In the latter case, the next point, i.e. the point with the next lower index is instead marked as $P_{linked}$, as shown in diagram b2).

Next, the tip shift vector is computed by taking the closest linked shape point, and orthogonally projecting it on the reference shape (interpolation), as shown in diagrams c1), d1), e1) and in diagrams c2), d2), and e2).

Once the tip shift vector is computed, the linked shape can be recalculated. The linked shape points that will be recalculated range from the computed linked shape hub point index to the end of the linked shape, including the tip of the linked shape.

Before the linked shape is recalculated, step S9 provides a check to make sure that the computed overlap region indices fall within the linked shape array size. If the check fails, the method proceeds to step S10, where the method is stopped, i.e. there is no matching of the linked shape with the reference shape.

There is an optional check in place, which for example, can be enabled/disabled in a configuration file of the visualization system 18, that checks for several points spread evenly on the computed overlap region OV if the linked shape and the reference shape actually are overlapping, i.e. linked shape points are within the error distance threshold of the reference shape. This optional check is useful to avoid that the method as described herein matches shapes that are not actually inside each other, but having tips close to each other. If this optional check is enabled and fails, the method will return to an error status, and no matching will take place.

If the check in step S9 is positive, then the method proceeds to step S11 in FIG. 4 in which, in the overlap region, the reference shape is copied to the linked shape so that, in the overlap region, the second sensed shape is visualized as matching the first sensed shape.

In more detail, in step S11, the lead-in part of the linked shape from the proximal end to the hub point H is skipped.

In the overlap region of an overlap of the linked shape and the reference shape, departing from the hub point H in distal direction, the reference shape along the overlap region is copied to the points along the linked shape in the overlap region. If the linked shape is sticking out of the reference shape, the protruding tip section points of the linked shape are translated with the computed tip shift vector. Linked shape portions outside the overlap region (OV), like the lead-in section are added to the overlap region reference shape portion to provide a full length visualization of the linked shape.

As a further aspect, in order to achieve a good alignment in terms of orientation, a Procrustes-based coordinate transformation of linked shape can be performed when the overlap region has been determined. The Procrustes transformation can be performed by taking overlapping reference and linked shape points and calculating a Procrustes matrix, and applying the matrix to the linked shape points. Using a Procrustes transformation limits the orientational inaccuracy of the linked shape. If the overlap region length is not known, a 'safe' number of points can be used for the Procrustes registration, starting from the overlap region start, and, if required, the optimal registration and overlap region length is determined. The Procrustes transformation could be done every n shape updates to limit the number of calculations, or triggered by a check of the registration validity. In the simplest form, the distance between the tip of the non-extending shape to the other shape can be used for that.

Further, duplicate points that are present in the recalculated linked shape are removed.

The result is a recalculated linked shape, which is matching with the reference shape in the overlap region OV.

Figure 10:
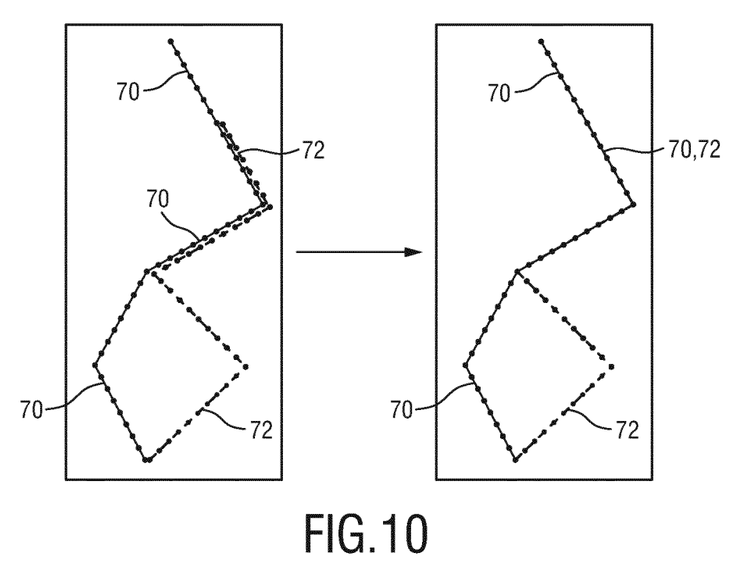
FIG. 10 illustrates an example of the result achieved by the method in FIG. 4.

FIG. 10 shows an example of the result of the method as described above, for a linked shape 70 and a reference shape 72. FIG. 10a) shows the situation of a misalignment between the linked shape 70 and the reference shape 72, and FIG. 10b) shows a perfect alignment of the linked shape 70 and the reference shape 72 in the overlap region.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program comprising program code means for causing a computer to carry out the steps of the visualization method as described herein may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A method of visualizing a first sensed shape of a first elongated device having a first length and a second sensed shape of a second elongated device having a second length, the first elongated device and the second elongated device being physically linked to one another over at least a part of the first and second lengths, the first sensed shape and the second sensed shape having been obtained independently of each other, the method comprising:
providing one of the first sensed shape or the second sensed shape as a reference shape and another of the first sensed shape or the second sensed shape as a linked shape;
determining along the reference shape and the linked shape an overlap region in which the reference shape and the linked shape should match due to a physical overlap of the first and second elongated devices in the overlap region; and
copying, in the overlap region, an overlap region reference shape portion of the reference shape to an overlap region linked shape portion of the linked shape so that, within the overlap region, the linked shape is visualized on a display as matching the reference shape.

2. The method of claim 1, further comprising adding linked shape portions outside the overlap region to the overlap region reference shape portion to provide a full length visualization of the linked shape.

3. The method of claim 1, further comprising performing a Procrustes-based coordinate transformation of the linked shape.

4. The method of claim 1, wherein providing one of the first sensed shape or the second sensed shape as a reference shape and the other of the first sensed shape or the second sensed shape as a linked shape comprises calculating a smallest first distance ($SD_{RefToLinked}$) from a tip of the reference shape to the linked shape, and calculating a smallest second distance ($SD_{LinkedToRef}$) from a tip of the linked shape to the reference shape.

5. The method of claim 4, wherein the overlap region reference shape portion is copied to the overlap region linked shape portion only when a smaller one of the smallest first and second distances ($SD_{RefToLinked}$, $SD_{LinkedToRef}$) is below a predetermined error threshold.

6. The method of claim 4, wherein determining the overlap region comprises determining a linked shape hub point index along the linked shape as a proximal starting point index of the overlap region with respect to the linked shape, and determining a reference shape hub point index as a proximal starting point index of the overlap region with respect to the reference shape.

7. The method of claim 1, wherein determining the overlap region comprises determining a tip shift vector, when a linked shape tip of the linked shape protrudes beyond a reference shape tip of the reference shape, and
wherein copying the overlap region reference shape portion to the overlap region linked shape portion comprises translating a linked shape tip portion of the linked shape according to the tip shift vector.

8. The method of claim 1, further comprising, before copying the overlap region reference shape portion to the overlap region linked shape portion, checking that all points of the linked shape in the determined overlap region fall within an array size of the linked shape.

9. The method of claim 1, further comprising, before copying the overlap region reference shape portion to the overlap region linked shape portion, checking that at least a part of the linked shape is within a threshold distance from the reference shape.

10. A system, comprising:
a first elongated device having a first length and a second elongated device having a second length, the first elongated device and the second elongated device being physically linked to one another in an overlap region over at least a part of the first and second lengths;
a shape sensing system for individually shape sensing the first elongated device and the second elongated device to provide a first sensed shape of the first elongated device and a second sensed shape of the second elongated device; and
a computer having a non-transitory storage medium for storing instructions that, when executed by the computer, cause the computer to:

provide one of the first sensed shave or the second sensed shape as a reference shape and another of the first sensed shape or the second sensed shape as a linked shape;

determine along the reference shape and the linked shape the overlap region in which the reference shape and the linked shape should match due to the physical linking of the first and second elongated devices in the overlap region; and copy, in the overlap region, an overlap region reference shape portion of the reference shape to an overlap region linked shape portion of the linked shape so that, within the overlap region, the linked shape is visualized on a display as matching the reference shape.

11. The system of claim 10, wherein the shape sensing system is configured as an optical shape sensing system.

12. The system of claim 11, wherein the optical shape sensing system comprises a first optical fiber associated with the first elongated device, and a second optical fiber associated with the second elongated device, wherein the shape sensing system senses the first and second optical fibers independently from one another.

13. The system of claim 10, wherein one of the first and second elongated devices is a catheter, and the other one is a guidewire at least partially inserted into the catheter.

14. The system of claim 10, wherein the instructions further cause the computer to perform a Procrustes-based coordinate transformation of the linked shape.

15. The system of claim 10, wherein one of the first sensed shape or the second sensed shape is provided as a reference shape and the other of the first sensed shape or the second sensed shape is identified as a linked shape by calculating a smallest first distance ($SD_{RefToLinked}$) from a tip of the reference shape to the linked shape, and calculating a smallest second distance ($SD_{LinkedToRef}$) from a tip of the linked shape to the reference shape.

16. The system of claim 15, wherein the overlap region reference shape portion is copied to the overlap region linked shape portion only when a smaller one of the smallest first and second distances ($SD_{RefToLinked}$, $SD_{LinkedToRef}$) is below a predetermined error threshold.

17. The system of claim 10, wherein the instructions further cause the computer to check that all points of the linked shape in the determined overlap region fall within an array size of the linked shape before copying the overlap region reference shape portion to the overlap region linked shape portion.

18. The system of claim 10, wherein the instructions further cause the computer to check that at least a part of the linked shape is within a threshold distance from the reference shape before copying the overlap region reference shape portion to the overlap region linked shape portion.

19. The system of claim 10, wherein the overlap region is determined by determining a tip shift vector, when a linked shape tip of the linked shape protrudes beyond a reference shape tip of the reference shape, and wherein the overlap region reference shape portion is copied to the overlap region linked shape portion by translating a linked shape tip portion of the linked shape according to the tip shift vector.

20. A non-transitory storage medium that stores instructions for visualizing on a display a first sensed shape of a first elongated device having a first length and a second sensed shape of a second elongated device having a second length, the first elongated device and the second elongated device being physically linked to one another in an overlap region over at least a part of the first and second lengths, the first sensed shape and the second sensed shape having been obtained independently of each other, wherein when executed by a computer, the instructions cause the computer to:

provide one of the first sensed shape or the second sensed shape as a reference shape and another of the first sensed shape or the second sensed shape as a linked shape;

determine along the reference shape and the linked shape the overlap region in which the reference shape and the linked shape should match due to the physical linking of the first and second elongated devices in the overlap region; and copy, in the overlap region, an overlap region reference shape portion of the reference shape to an overlap region linked shape portion of the linked shape so that, within the overlap region, the linked shape is visualized on the display as matching the reference shape.

* * * * *